(12) United States Patent
Holl et al.

(10) Patent No.: US 10,802,123 B2
(45) Date of Patent: Oct. 13, 2020

(54) METHOD AND SYSTEM FOR FAILURE DETECTION OF A MECHANICAL ULTRASOUND TRANSDUCER ASSEMBLY

(71) Applicant: General Electric Company, Schenectady, NY (US)

(72) Inventors: Stefan Holl, Zipf (AT); Franz Steinbacher, Zipf (AT)

(73) Assignee: GENERAL ELECTRIC COMPANY, Schenectady, NY (US)

(*) Notice: Subject to any disclaimer, the term of this patent is extended or adjusted under 35 U.S.C. 154(b) by 560 days.

(21) Appl. No.: 15/725,412

(22) Filed: Oct. 5, 2017

(65) Prior Publication Data

US 2019/0107612 A1 Apr. 11, 2019

(51) Int. Cl.
*G01S 7/52* (2006.01)
*A61B 8/00* (2006.01)
(Continued)

(52) U.S. Cl.
CPC ........ *G01S 7/52004* (2013.01); *A61B 8/0841* (2013.01); *A61B 8/4461* (2013.01); *A61B 17/3403* (2013.01); *B06B 1/0607* (2013.01); *G01S 7/5205* (2013.01); *G01S 7/52079* (2013.01); *G01S 15/894* (2013.01); *G01S 15/8913* (2013.01); *G01S 15/8925* (2013.01); *G10K 11/355* (2013.01); *A61B 8/4444* (2013.01); *A61B 8/483* (2013.01); *A61B 8/5207* (2013.01); *A61B 2017/3413* (2013.01); *A61B 2090/0808* (2016.02)

(58) Field of Classification Search
CPC ............... G01S 7/52004; G01S 7/5205; G01S 7/52079; G01S 15/8913; G01S 15/8925; G01S 15/894; G10K 11/355; A61B 8/4461; A61B 8/0841; A61B 17/3403; A61B 2017/3413; A61B 2090/0808; A61B 8/483; A61B 8/5207; A61B 8/4444; B06B 1/0607
See application file for complete search history.

(56) References Cited

U.S. PATENT DOCUMENTS

| | | | |
|---|---|---|---|
| 2003/0011285 A1* | 1/2003 | Ossmann | G01S 15/892 310/334 |
| 2006/0241426 A1* | 10/2006 | Fujii | A61B 8/4281 600/437 |

(Continued)

*Primary Examiner* — Daniel Pihulic
(74) *Attorney, Agent, or Firm* — McAndrews, Held & Malloy, Ltd.; Jacob Groethe; David Bates

(57) ABSTRACT

An ultrasound probe may include a mechanical transducer and a probe housing. The mechanical transducer may be rotatable about an axis. The mechanical transducer may be operable to acquire ultrasound image data at one or more rotational positions of a plurality of rotational positions. The probe housing may include a probe cap covering the mechanical transducer. The mechanical transducer may be directed toward the probe cap at each of the plurality of rotational positions. The probe cap may include a defined structure having a first thickness and a remainder portion having a second thickness different than the first thickness. In various embodiments, at least a portion of the defined structure is at a center section of the probe cap corresponding with a center rotational position of the mechanical transducer.

19 Claims, 8 Drawing Sheets

(51) Int. Cl.
  *A61B 8/08* (2006.01)
  *A61B 17/34* (2006.01)
  *B06B 1/06* (2006.01)
  *G01S 15/89* (2006.01)
  *G10K 11/35* (2006.01)
  *A61B 90/00* (2016.01)

(56) References Cited

U.S. PATENT DOCUMENTS

2019/0107612 A1\* 4/2019 Holl .................... G01S 7/52004
2019/0216438 A1\* 7/2019 Song ..................... A61B 8/461

\* cited by examiner

METHOD AND SYSTEM FOR FAILURE DETECTION OF A MECHANICAL ULTRASOUND TRANSDUCER ASSEMBLY

FIELD

Certain embodiments relate to mechanical ultrasound transducer assemblies. More specifically, certain embodiments relate to a method and system for detecting a failure of a mechanical ultrasound transducer assembly by analyzing artifacts in ultrasound images of a probe cap having a defined structure.

BACKGROUND

Ultrasound imaging is a medical imaging technique for imaging organs and soft tissues in a human body. Ultrasound imaging uses real time, non-invasive high frequency sound waves to produce a two-dimensional (2D) image and/or a three-dimensional (3D) image.

Mechanical ultrasound transducer assemblies include a movable transducer within a probe housing. The movable transducer emits ultrasound waves through a probe cap of the probe housing. For certain applications, it may be desirable to known the precise position of the movable transducer. For example, knowledge of the position of the movable transducer with respect to a biopsy guide attached to the ultrasound probe is crucial to perform a mechanically guided biopsy. For such applications, the movable transducer is typically desired at a center position and the biopsy guide is fixed to the probe housing so that the biopsy needle resides in the center ultrasound B-plane given by the ultrasound transducer.

FIG. 1 illustrates a front perspective view of an exemplary ultrasound probe 10 having a biopsy guide 20 as known in the art. Referring to FIG. 1, the ultrasound probe 10 may include a probe housing 14 having a probe cap 12. A biopsy guide 20 may be attached to the probe housing 14 such that a needle 22 may be guided for insertion in a target 30 at a fixed orientation defined by the biopsy guide 20.

FIG. 2 illustrates a side cross-sectional view of an exemplary ultrasound probe 10 having a mechanical ultrasound transducer 11 as known in the art. Referring to FIG. 2, the ultrasound probe 10, shown perpendicular to the ultrasound probe 10 of FIG. 1, includes a probe housing 14 having a probe cap 12. A mechanical transducer 11 disposed within the probe housing 14 and/or probe cap 12 is rotatable in directions 15 by a motor driving gears, belts, or rope, for example, to rotate hub or axis 13. For example, the mechanical transducer 11 is typically movable approximately 120 to 150 degrees in a single plane. Referring to FIGS. 1 and 2, it may be desirable to position the mechanical ultrasound transducer 11 at a center position to capture ultrasound image data of the needle 22 as guided by the biopsy guide 20. The mechanical transducer 11 may not acquire ultrasound image data of the needle 22 if the transducer 11 is positioned off-center as shown in FIG. 2.

Conventional mechanical ultrasound transducer assemblies are unable to determine the rotational position of the ultrasound transducer directly at the transducer elements. Instead, the ultrasound transducer rotational position is typically determined indirectly by a sensor located on the drive-motor or on the gear-drive. In the event of a mechanical or electrical failure, the rotational position of the ultrasound transducer elements is unknown. For example, the gears, drive belts, and/or rope for pivoting the hub or axis may break and/or sensors may malfunction in some cases. Consequently, an ultrasound operator may unknowingly use a defective ultrasound probe while performing a guided biopsy or other examination calling for a known ultrasound transducer position.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for detecting a failure of a mechanical ultrasound transducer assembly by analyzing artifacts in ultrasound images of a probe cap having a defined structure, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Figure 1:
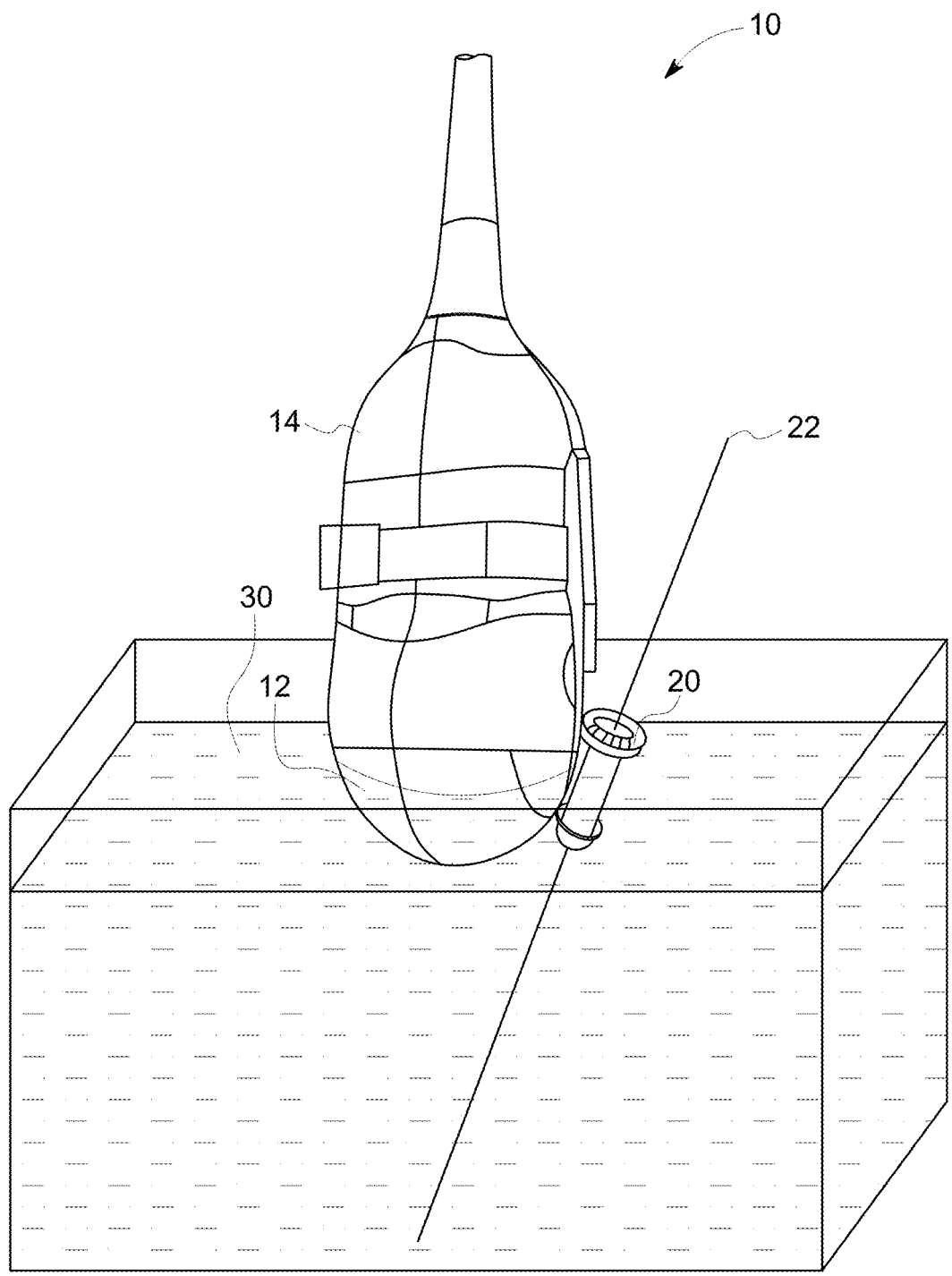
FIG. 1 illustrates a front perspective view of an exemplary ultrasound probe having a biopsy guide as known in the art.
Figure 2:
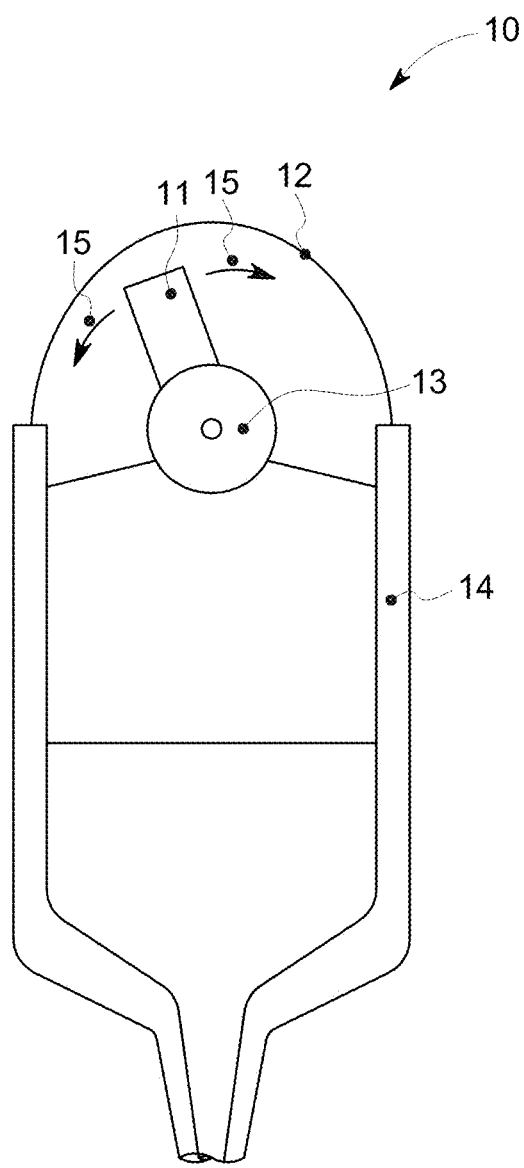
FIG. 2 illustrates a side cross-sectional view of an exemplary ultrasound probe having a mechanical ultrasound transducer as known in the art.

Certain embodiments may be found in a method and system for detecting a failure of a mechanical ultrasound transducer assembly by analyzing artifacts in ultrasound images of a probe cap having a defined structure. For example, various aspects have the technical effect of detecting a transition between different probe cap thicknesses in ultrasound image artifacts. The presence, lack of presence, and/or position of the ultrasound image artifacts in the ultrasound image data may be analyzed to determine the position of the mechanical ultrasound transducer and/or whether the mechanical ultrasound transducer assembly has failed and/or malfunctioned. Various embodiments have the technical effect of automatically disabling a mechanical ultrasound transducer assembly that has malfunctioned and/or failed. Certain embodiments have the technical effect of alerting an ultrasound operator of a malfunction and/or failure of a mechanical ultrasound transducer assembly.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments of the present disclosure. The following detailed description is, therefore, not to be taken in a limiting sense, and the scope of the present disclosure is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "an embodiment," "one embodiment," "a representative embodiment," "an exemplary embodiment," "various embodiments," "certain embodiments," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode, CF-mode and/or sub-modes of CF such as TVI, Angio, B-flow, BMI, BMI_Angio, and in some cases also MM, CM, PW, TVD, CW where the "image" and/or "plane" includes a single beam or multiple beams.

Furthermore, the term processor or processing unit, as used herein, refers to any type of processing unit that can carry out the required calculations needed for the disclosure, such as single or multi-core: CPU, Graphics Board, DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 3.

Figure 3:
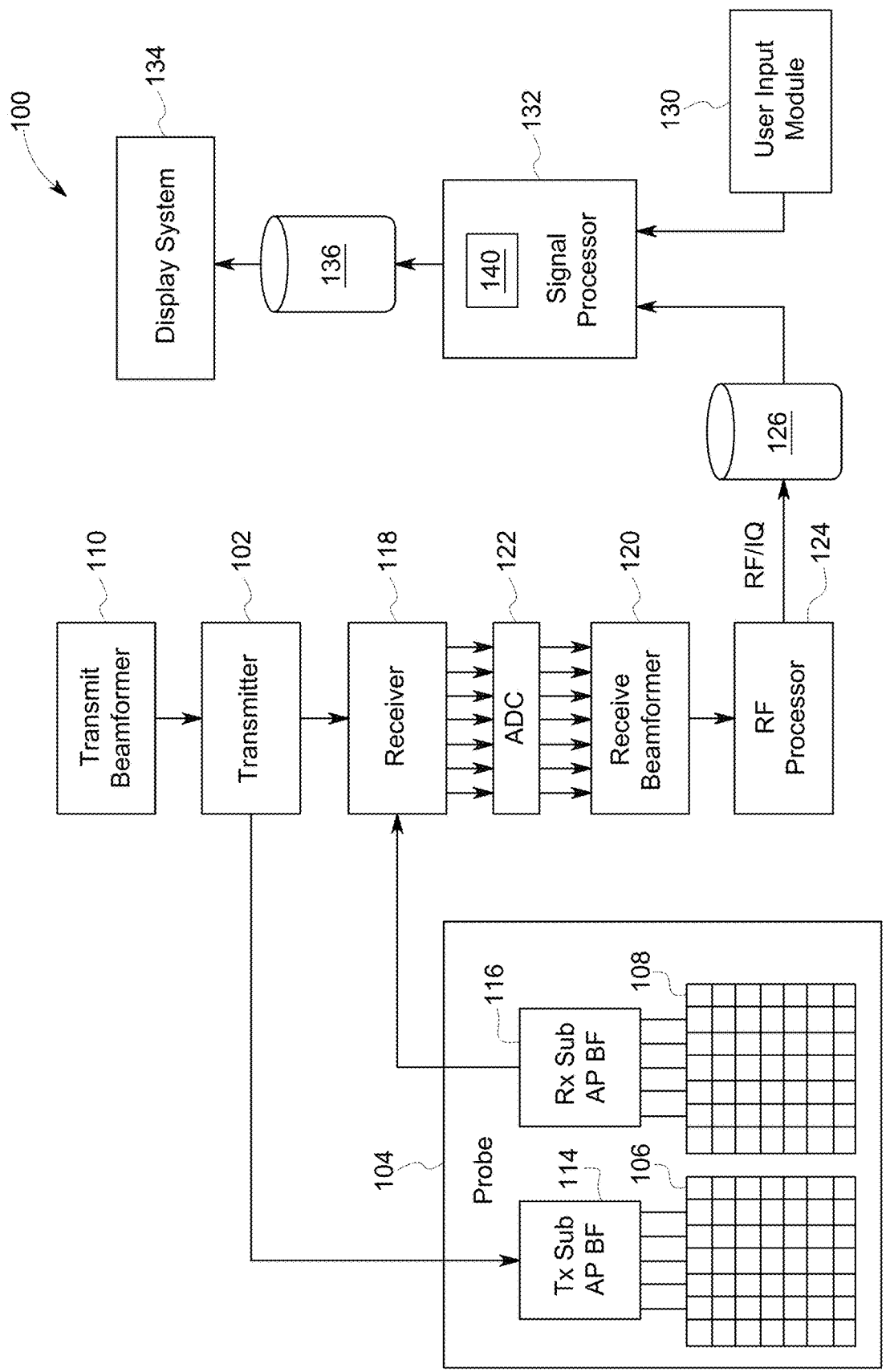
FIG. 3 is a block diagram of an exemplary ultrasound system that is operable to detect a failure of a mechanical ultrasound transducer assembly by analyzing artifacts in ultrasound images of a probe cap having a defined structure, in accordance with various embodiments.

FIG. 3 is a block diagram of an exemplary ultrasound system 100 that is operable to detect a failure of a mechanical ultrasound transducer assembly 104 by analyzing artifacts in ultrasound images of a probe cap having a defined structure, in accordance with various embodiments. Referring to FIG. 3, there is shown an ultrasound system 100. The ultrasound system 100 comprises a transmitter 102, an ultrasound probe 104, a transmit beamformer 110, a receiver 118, a ADC 122, a receive beamformer 120, a RF processor 124, a RF/IQ buffer 126, a user input module 130, a signal processor 132, an image buffer 136, and a display system 134.

The transmitter 102 may comprise suitable logic, circuitry, interfaces and/or code that may be operable to drive an ultrasound probe 104. The ultrasound probe 104 may comprise a two dimensional (2D) array of piezoelectric elements mounted on a transducer assembly movable in a single plane. For example, the mechanical transducer assembly may be movable approximately 120 to 150 degrees by a motor driving gears, belts, and/or rope to pivot an axis or hub of the movable transducer assembly. The ultrasound probe 104 may comprise a group of transmit transducer elements 106 and a group of receive transducer elements 108, that normally constitute the same elements mounted on the mechanical transducer assembly. The mechanical transducer assembly may be disposed in oil within a probe body having a probe cap. As described below with reference to FIGS. 4-10, the probe cap includes a defined structure having a thickness different from the thickness of other portions of the probe cap. The group of transmit transducer elements 106 may emit ultrasonic signals through the oil and probe cap and into a target. The defined structure may be positioned on an inside surface of the probe cap such that a distance between the group of transmit transducer elements 106 and the inside surface of the probe cap at the defined structure is different than a distance between the group of transmit transducer elements 106 and the inside surface of the remainder of the probe cap. The defined structure in the probe cap may cause a defined reflection signal of the ultrasound waves that may be evaluated by the ultrasound system 100 to determine the rotational position of the mechanical transducer assembly as described in more detail below. Additionally and/or alternatively, the defined reflection signal may be presented in an ultrasound image at the display system 134 such that an ultrasound operator may visually confirm the rotational position of the mechanical transducer assembly.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive and demodulate the signals from the receive sub-aperture beamformer 116. The demodulated analog signals may be communicated to one or more of the plurality of A/D converters 122.

The plurality of A/D converters 122 may comprise suitable logic, circuitry, interfaces and/or code that may be operable to convert the demodulated analog signals from the receiver 118 to corresponding digital signals. The plurality of A/D converters 122 are disposed between the receiver 118 and the receive beamformer 120. Notwithstanding, the disclosure is not limited in this regard. Accordingly, in some embodiments, the plurality of A/D converters 122 may be integrated within the receiver 118.

The receive beamformer 120 may comprise suitable logic, circuitry, interfaces and/or code that may be operable to perform digital beamforming processing to, for example, sum the delayed channel signals received from the plurality of A/D converters 122 and output a beam summed signal. The resulting processed information may be converted back to corresponding RF signals. The corresponding output RF signals that are output from the receive beamformer 120 may be communicated to the RF processor 124. In accordance with some embodiments, the receiver 118, the plurality of A/D converters 122, and the beamformer 120 may be integrated into a single beamformer, which may be digital.

The RF processor 124 may comprise suitable logic, circuitry, interfaces and/or code that may be operable to demodulate the RF signals. In accordance with an embodiment, the RF processor 124 may comprise a complex demodulator (not shown) that is operable to demodulate the RF signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The user input module 130 may be utilized to input patient data, surgical instrument data, scan parameters, settings, configuration parameters, change scan mode, and the like. In an exemplary embodiment, the user input module 130 may be operable to configure, manage and/or control operation of one or more components and/or modules in the ultrasound system 100. In this regard, the user input module 130 may be operable to configure, manage and/or control operation of transmitter 102, the ultrasound probe 104, the transmit beamformer 110, the receiver 118, the receive beamformer 120, the RF processor 124, the RF/IQ buffer 126, the user input module 130, the signal processor 132, the image buffer 136, and/or the display system 134.

The signal processor 132 may comprise suitable logic, circuitry, interfaces and/or code that may be operable to process ultrasound scan data (i.e., RF signal data or IQ data pairs) for generating an ultrasound image for presentation on a display system 134. In various embodiments, the ultrasound image presented at the display system 134 may include artifacts in the close range (e.g., at a top of a B-mode image) corresponding with reflections from the probe cap of the ultrasound probe 104. For example, the defined structure in the probe cap of the ultrasound probe 104 causes a defined reflection signal from a portion of the ultrasound waves directed at the defined structure of the probe cap. The portions of the probe cap not having the defined structure provide a different reflection signal than the defined reflection signal. The different reflection signals may create distinguishable artifacts in the close range of an ultrasound image as described with respect to FIGS. 11 and 12 below. In an exemplary embodiment, an ultrasound operator may visually confirm the rotational position of the mechanical transducer assembly based on the artifacts shown in the close range of the ultrasound image presented at the display system 134.

The signal processor 132 is operable to perform one or more processing operations according to a plurality of selectable ultrasound modalities on the acquired ultrasound scan data. In an exemplary embodiment, the signal processor 132 may be operable to perform compounding, motion tracking, and/or speckle tracking. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation.

The ultrasound system 100 may be operable to continuously acquire ultrasound scan data at a frame rate that is suitable for the imaging situation in question. Typical frame rates range from 20-70 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several seconds' worth of frames of ultrasound scan data. The frames of ultrasound scan data are stored in a manner to facilitate retrieval thereof according to its order or time of acquisition. The image buffer 136 may be embodied as any known data storage medium.

The signal processor 132 may include a mechanical transducer failure detection module 140 that comprises suitable logic, circuitry, interfaces and/or code that may be operable to process ultrasound image data to determine a rotational position of the mechanical ultrasound transducer within the probe 104. For example, the defined structure of the probe cap of the ultrasound probe 104 produces a defined reflection signal of ultrasonic signals transmitted from the mechanical transducer. As described below with respect to FIGS. 4-10, the defined structure may include grooves, protrusions, and/or portions of the probe cap having a thickness different from the thickness of the remainder of the probe cap. As described below with respect to FIGS. 11 and 12, the defined reflections of the defined structure in the probe cap produce artifacts distinguishable from the artifacts produced by the remainder of the probe cap. Accordingly, the mechanical transducer failure detection module 140 may detect the different artifacts and/or the transitions between different sets of artifacts. As an example, the mechanical transducer failure detection module 140 may apply image detection techniques and/or machine learning techniques to detect whether artifacts corresponding to defined structure of the probe cap are present in the ultrasound image data and the position of any detected artifacts.

In various embodiments, the mechanical transducer failure detection module 140 may include one or more deep neural networks and/or utilize any suitable form of machine learning processing functionality to detect the presence and position of artifacts associated with the defined structure in the probe cap of the ultrasound probe 104. For example, the mechanical transducer failure detection module 140 may be made up of an input layer, an output layer, and one or more hidden layers in between the input and output layers. Each of the layers may be made up of a plurality of processing nodes that may be referred to as neurons. For example, the input layer may have a neuron for each pixel or a group of pixels from an ultrasound image or at least the close range (e.g., at a top of a B-mode image) of the ultrasound image. The output layer may have a neuron corresponding to a correct position of detected defined structure artifacts and one or more neurons corresponding with incorrect position(s) and/or no detected defined structure artifacts. Each neuron of each layer may perform a processing function and pass the processed ultrasound image information to one of a plurality of neurons of a downstream layer for further processing. As an example, neurons of a first layer may learn to recognize edges of artifact in the ultrasound image data. The neurons of a second layer may learn to recognize artifact types based on the detected edges from the first layer. The neurons of a third layer may learn the appropriate position of the recognized artifact types in the ultrasound image data. The processing performed by the mechanical transducer failure detection module 140 deep neural network may provide a determination of whether the mechanical transducer is appropriately positioned with a high degree of probability.

The mechanical transducer failure detection module 140 may comprise suitable logic, circuitry, interfaces and/or code that may be operable to disable the ultrasound probe 104 and/or to provide a transducer failure notification in response to a determination that the mechanical transducer is in an incorrect rotational position. For example, the mechanical transducer failure detection module 140 may shut off power provided to the ultrasound probe 104. As another example, the mechanical transducer failure detection module 140 may control the operation of the transmitter 102, the ultrasound probe 104, the transmit beamformer 110, the receiver 118, and/or the receive beamformer 120 to prevent the transmission of ultrasonic signals and/or the processing of any received echoes. In various embodiments, the mechanical transducer failure detection module 140 may provide a visual and/or audible notification to alert an ultrasound operator of the malfunctioning mechanical transducer of the ultrasound probe 104. By providing alerts and/or disabling the probe 104, the mechanical transducer failure detection module 140 may allow an ultrasound operator to replace the ultrasound probe 104 prior to or early on in a procedure if a mechanical and/or electrical failure of the mechanical ultrasound transducer is detected.

Figure 4:
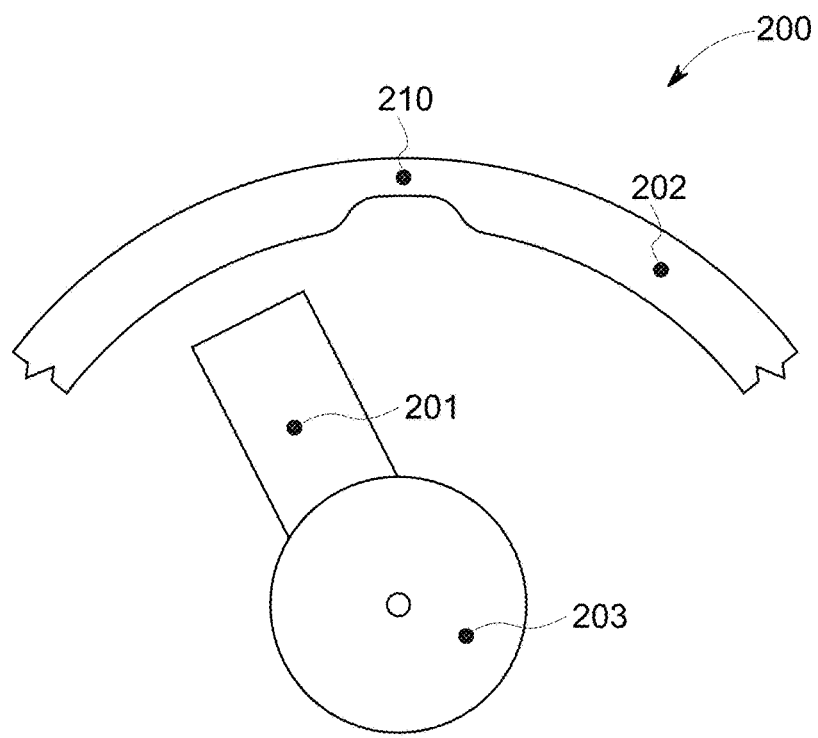
FIG. 4 illustrates a side cross-sectional view of an exemplary ultrasound probe having a probe cap with a defined structure, in accordance with a first embodiment.

FIG. 4 illustrates a side cross-sectional view of an exemplary ultrasound probe 200 having a probe cap 202 with a defined structure 210, in accordance with a first embodiment. Referring to FIG. 4, the ultrasound probe 200 comprises a mechanical transducer 201 disposed in oil within a probe cap 202. The mechanical transducer 201 is rotatable approximately 120 to 150 degrees in a single plane by a motor driving gears, belts, or rope, for example, to rotate hub or axis 203. The probe cap 202 comprises a defined structure 210 that may be positioned at a center of the inside surface of the probe cap 202. The probe cap 202 may have a uniform thickness with the exception of the thickness at the defined structure 210. For example, as shown in FIG. 4, the defined structure 210 may be a groove having a smaller thickness than the remainder of the probe cap 202. The groove 210 may extend through at least a portion of the probe cap at a position corresponding with a center ultrasound image acquisition plane of the mechanical transducer 201. The different thickness of the defined structure 210 and the remainder of the probe cap 202 causes distinguishable artifacts to be provided in a close range of acquired ultrasound image data if the mechanical transducer 201 is pointed in the direction of the defined structure 210. For example, if the mechanical transducer 201 is at a center rotational position, the acquired ultrasound data would include artifacts representative of the defined structure 210 in the center close range position of a corresponding ultrasound image.

Figure 11:
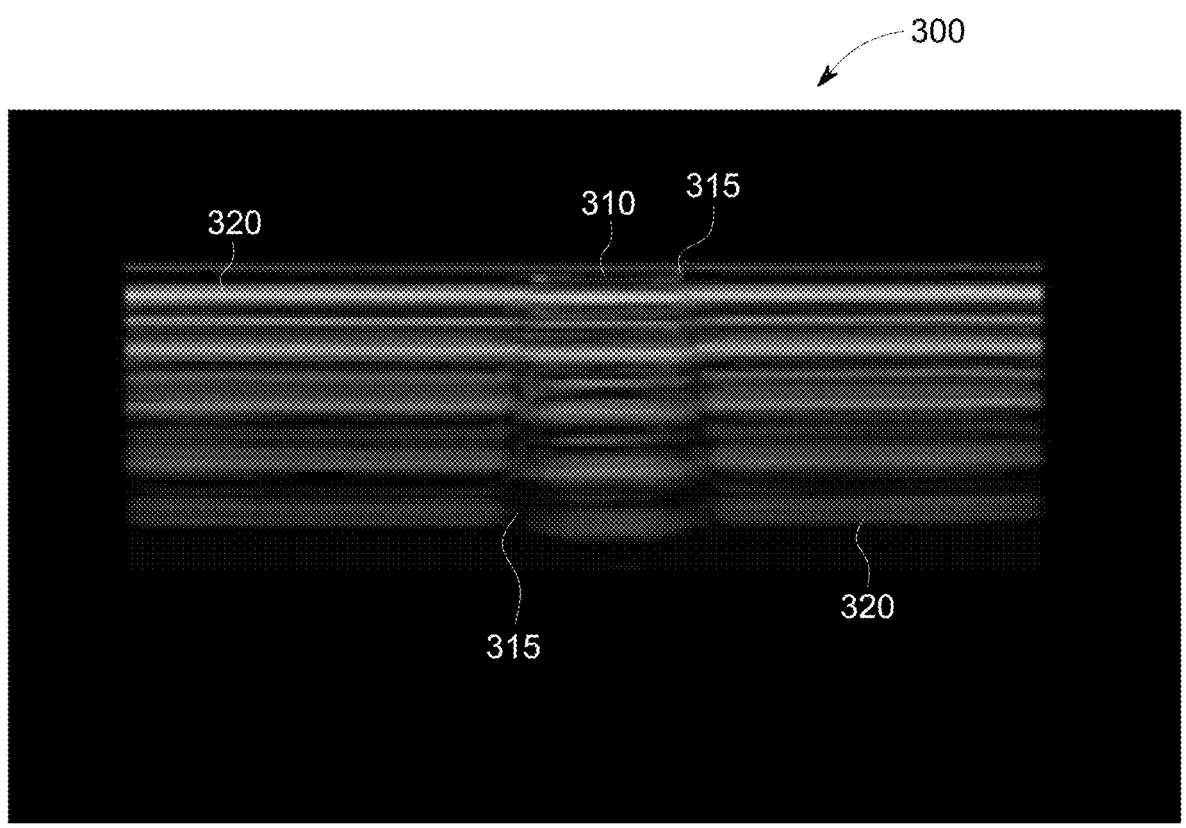
FIG. 11 illustrates an exemplary ultrasound image having artifacts showing a defined structure of a probe cap, in accordance with various embodiments.

FIG. 11 illustrates an exemplary ultrasound image 300 having artifacts 310 showing a defined structure 210 of a probe cap 202, in accordance with various embodiments. Referring to FIG. 11, a transition 315 between two generally uniform sets of artifacts 310, 320 are shown. The artifacts 310 at the central portion may correspond with the defined structure 210 having a first thickness. The generally uniform artifacts 320 at the outer portions of the ultrasound image 300 may correspond with the remainder of the probe cap 202 having a second thickness different from the first thickness. The ultrasound image 300 may be presented at a display system 134 for analysis by an ultrasound operator and/or processed by a mechanical transducer failure detection module 140 to determine whether the mechanical transducer 201 is correctly oriented at a central rotational position. The mechanical transducer failure detection module 140 and/or ultrasound operator may determine that the mechanical transducer 201 has malfunctioned if the artifacts 310 are not shown in the ultrasound image 300 and/or if the artifacts 310 are not shown at the appropriate position in the ultrasound image 300. Referring again to FIG. 4, for example, the mechanical transducer 201 positioned as shown may not acquire image data having the artifacts 310 corresponding with the defined structure 210 because the mechanical transducer 201 is not positioned at a center rotational position.

The ultrasound probe 200 illustrated in FIG. 4 shares various characteristics with the ultrasound probe 104 illustrated in FIG. 3 as described above.

Figure 5:
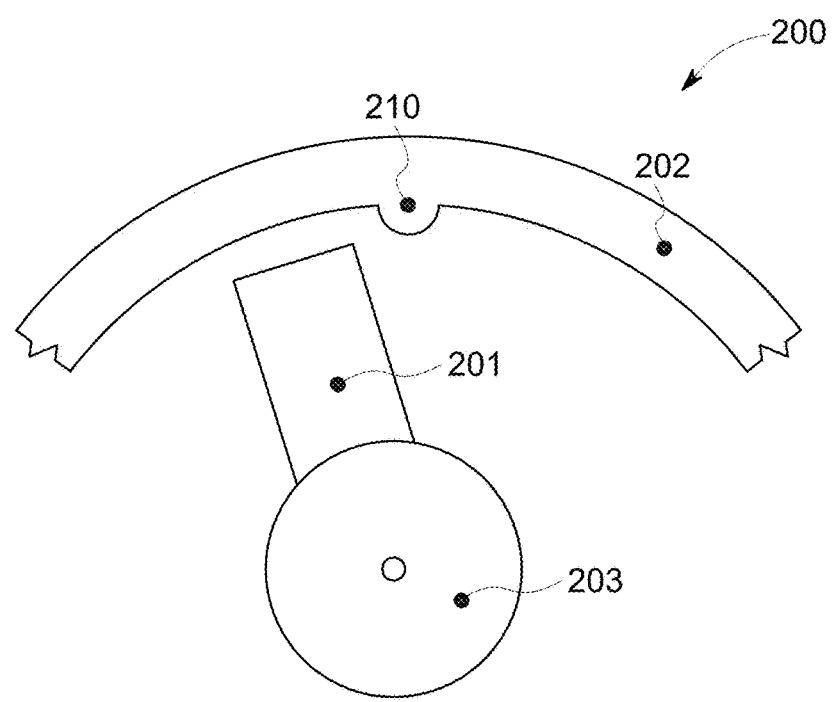
FIG. 5 illustrates a side cross-sectional view of an exemplary ultrasound probe having a probe cap with a defined structure, in accordance with a second embodiment.

FIG. 5 illustrates a side cross-sectional view of an exemplary ultrasound probe 200 having a probe cap 202 with a defined structure 210, in accordance with a second embodiment. Referring to FIG. 5, the ultrasound probe 200 comprises a mechanical transducer 201 disposed in oil within a probe cap 202 and rotatable about a hub or axis 203. The probe cap 202 comprises a defined structure 210, such as the protrusion illustrated in FIG. 5, that may extend across at least a portion of the inside surface of the probe cap 202 at a position corresponding with a center ultrasound image acquisition plane of the mechanical transducer 201. The defined structure 210 may have a first thickness and the remainder of the probe cap 202 may have a second, uniform thickness smaller than the first thickness of the defined structure 210 that causes distinguishable artifacts to be provided in a close range of acquired ultrasound image data if the mechanical transducer 201 is pointed in the direction of the defined structure 210. Referring again to FIG. 11, the artifacts 310 at the central portion may correspond with the protrusion 210 having a larger thickness and the generally uniform artifacts 320 at the outer portions of the ultrasound image 300 may correspond with the remainder of the probe cap 202 having a smaller thickness. The mechanical transducer failure detection module 140 and/or ultrasound operator may determine that the mechanical transducer 201 has malfunctioned if the artifacts 310 are not shown in the ultrasound image 300 and/or if the artifacts 310 are not shown at the appropriate position in the ultrasound image 300.

The ultrasound probe 200 illustrated in FIG. 5 shares various characteristics with the ultrasound probe 104 illustrated in FIG. 3 as described above.

Figure 6:
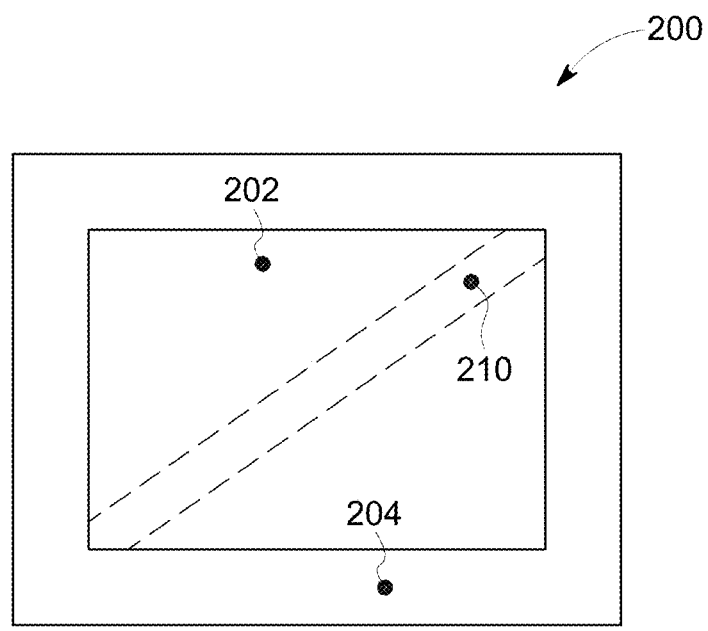
FIG. 6 illustrates a top elevation view of an exemplary ultrasound probe having a probe cap with a defined structure, in accordance with a third embodiment.

FIG. 6 illustrates a top elevation view of an exemplary ultrasound probe 200 having a probe cap 202 with a defined structure 210, in accordance with a third embodiment. Referring to FIG. 6, the ultrasound probe 200, shown perpendicular to the ultrasound probes 200 of FIGS. 4 and 5, comprises a probe housing 204 including a probe cap 202 having a defined structure 210. A mechanical transducer (not shown) may be disposed in oil within the probe cap 202 and rotatable about a hub or axis (not shown) in up and down directions with reference to the orientation of FIG. 6. The probe cap 202 comprises a defined structure 210, such as a groove or protrusion, extending diagonally across at least a portion of the probe cap 202 in the ultrasound image acquisition plane of the mechanical transducer 201. The defined structure 210 may have a first thickness and the remainder of the probe cap 202 may have a second, uniform thickness different from the first thickness of the defined structure 210 that causes distinguishable artifacts to be provided in a close range of acquired ultrasound image data. In the embodiment of FIG. 6, the diagonal orientation of the defined structure 210 ensures that the mechanical transducer captures ultrasound image data having artifacts 310 corresponding to the defined structure 210. For example, if the mechanical transducer has a center rotational position, the artifacts 310 created by the defined structure 210 may appear at the center, close range position in an ultrasound image 300 as shown in FIG. 11. As another example, if the mechanical transducer is rotated up or down from the center rotational position, the artifacts 310 created by the defined structure 210 may appear at left or right close range positions in the ultrasound image 300. The mechanical transducer failure detection module 140 and/or ultrasound operator may determine the rotational position of the mechanical transducer 201 based on the detected position of the artifacts 310 in the ultrasound image 300.

The ultrasound probe 200 illustrated in FIG. 6 shares various characteristics with the ultrasound probe 104 illustrated in FIG. 3 as described above.

Figure 7:
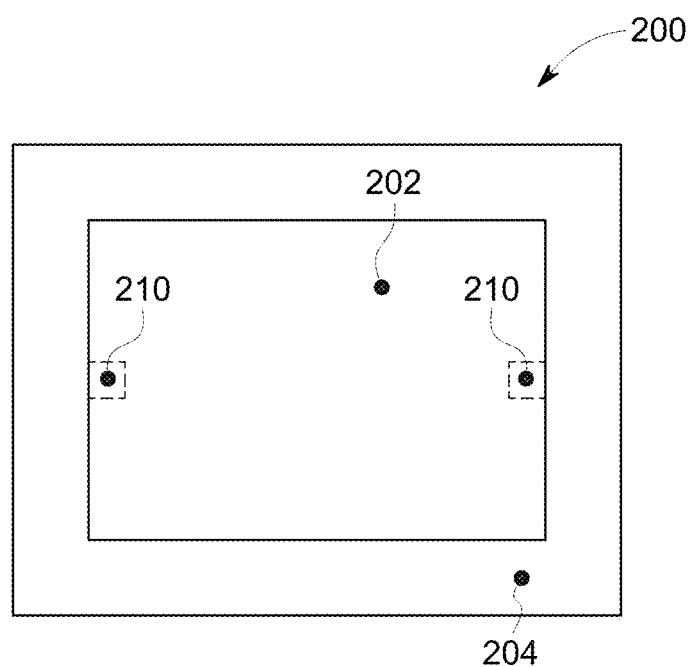
FIG. 7 illustrates a top elevation view of an exemplary ultrasound probe having a probe cap with a defined structure, in accordance with a fourth embodiment.

FIG. 7 illustrates a top elevation view of an exemplary ultrasound probe 200 having a probe cap 202 with a defined structure 210, in accordance with a fourth embodiment. Referring to FIG. 7, the ultrasound probe 200, shown perpendicular to the ultrasound probes 200 of FIGS. 4 and 5, comprises a probe housing 204 including a probe cap 202 having a defined structure 210. A mechanical transducer (not shown) may be disposed in oil within the probe cap 202 and rotatable about a hub or axis (not shown) in up and down directions with reference to the orientation of FIG. 7. The probe cap 202 comprises defined structures 210, such as grooves or protrusions, positioned at outer edges of a center ultrasound image acquisition plane of the mechanical transducer 201. The defined structures 210 may have a first thickness and the remainder of the probe cap 202 may have a second, uniform thickness different from the first thickness of the defined structures 210 that causes distinguishable artifacts to be provided in a close range of acquired ultrasound image data if the mechanical transducer 201 is pointed in the direction of the defined structure 210.

Figure 12:
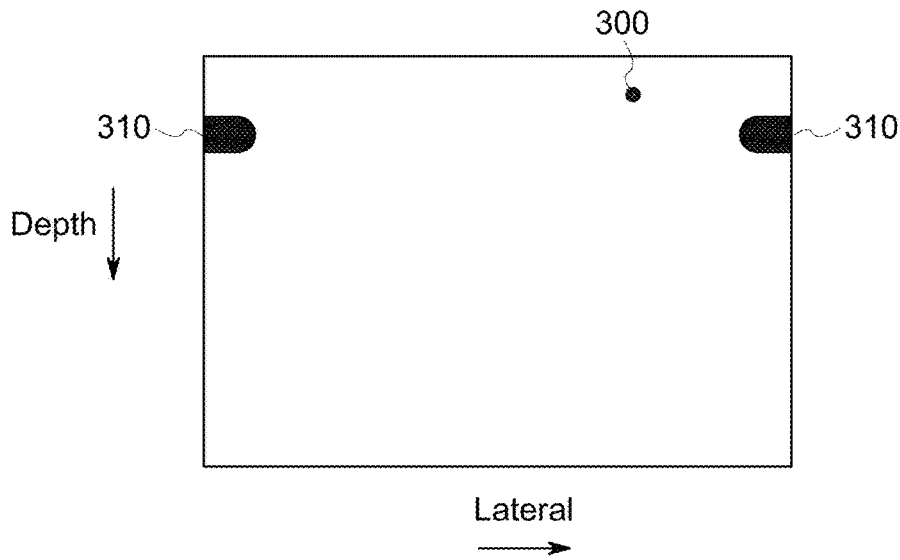
FIG. 12 illustrates an exemplary ultrasound image having artifacts showing a defined structure of a probe cap, in accordance with various embodiments.

FIG. 12 illustrates an exemplary ultrasound image 300 having artifacts 310 showing a defined structure 210 of a probe cap 202, in accordance with various embodiments. Referring to FIG. 12, artifacts 310 are shown in a close range at outer edges of an ultrasound image 300. The artifacts 310 at the outer edges of the ultrasound image 300 may correspond with the defined structure 210 having a first thickness. In various embodiments, the image area between the artifacts 310 may include generally uniform artifacts corresponding with the remainder of the probe cap 202 having a second thickness different from the first thickness. The ultrasound image 300 may be presented at a display system 134 for analysis by an ultrasound operator and/or processed by a mechanical transducer failure detection module 140 to determine whether the mechanical transducer 201 is correctly oriented at a central rotational position. The mechanical transducer failure detection module 140 and/or ultrasound operator may determine that the mechanical transducer 201 has malfunctioned if the artifacts 310 created by the defined structures 210 of FIG. 7, for example, are not shown in the ultrasound image 300 and/or if the artifacts 310 are not shown at the appropriate position in the ultrasound image 300.

The ultrasound probe 200 illustrated in FIG. 7 shares various characteristics with the ultrasound probe 104 illustrated in FIG. 3 as described above.

Figure 8:
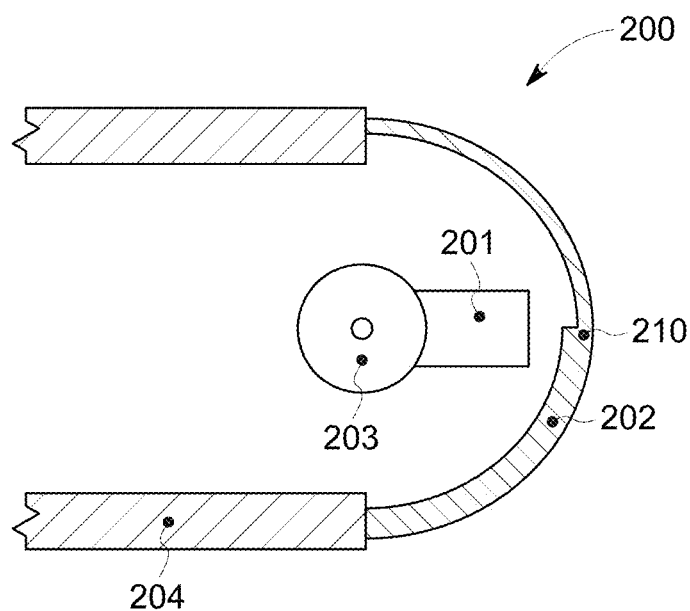
FIG. 8 illustrates a side cross-sectional view of an exemplary ultrasound probe having a probe cap with a defined structure, in accordance with a fifth embodiment.
Figure 9:
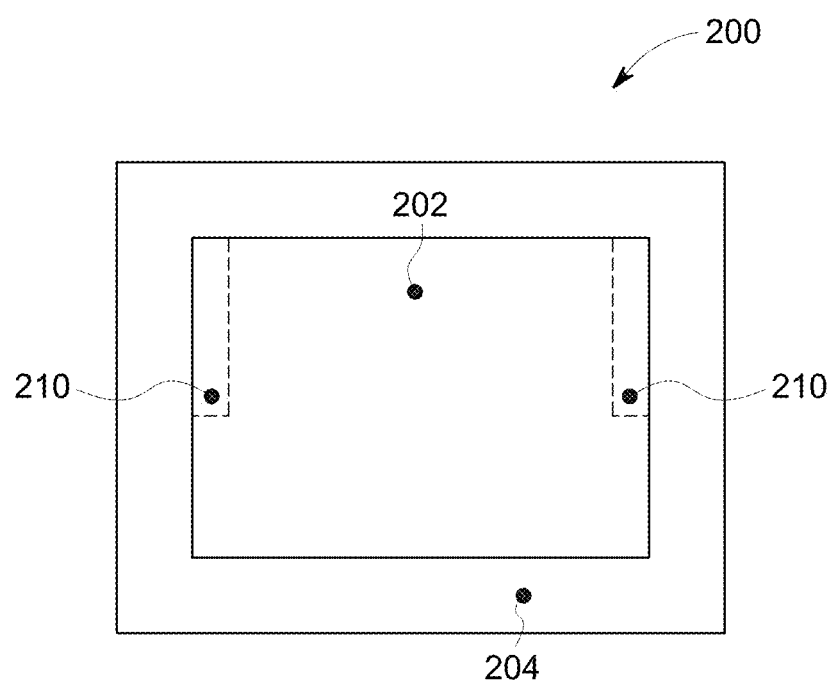
FIG. 9 illustrates a top elevation view of an exemplary ultrasound probe having a probe cap with a defined structure, in accordance with the fifth embodiment.

FIG. 8 illustrates a side cross-sectional view of an exemplary ultrasound probe 200 having a probe cap 202 with a defined structure 210, in accordance with a fifth embodiment. FIG. 9 illustrates a top elevation view of an exemplary ultrasound probe 200 having a probe cap 202 with a defined structure 210, in accordance with the fifth embodiment. The ultrasound probe 200 in FIG. 8 is shown perpendicular to the ultrasound probe 200 of FIG. 9. Referring to FIGS. 8 and 9, the ultrasound probe 200 comprises a mechanical transducer 201 disposed in oil within a probe cap 202 and rotatable about a hub or axis 203. The probe cap 202 comprises defined structures 210, such as protrusions or grooves, extending across outer edges of approximately one half of the probe cap 202. The defined structures 210 of the probe cap 202 may be a first thickness and the remainder of the probe cap 202 may be a second, generally uniform thickness different from the thickness of the defined structures 210. The defined structures 210 may be at outer edges of approximately half of the ultrasound image acquisition planes of the mechanical transducer 201 extending from a position corresponding with a center ultrasound image acquisition plane of the mechanical transducer 201 toward one end of the probe cap 202 along the rotational direction of the mechanical transducer 201 as shown in FIG. 9. The defined structures 210 cause distinguishable artifacts to be provided in a close range of acquired ultrasound image data if the mechanical transducer 201 is directed at the transition point at the center ultrasound image acquisition plane between the defined structures 210 at the edges on a first approximately half of the probe cap 202 and the edges not having the defined structures on a second approximately half of the probe cap 202.

Referring again to FIG. 12, the artifacts 310 at the outer edges of the ultrasound image 300 may correspond with a transition from the defined structure 210 having a first thickness to the approximately half of the ultrasound image acquisition planes of the mechanical transducer 201 at the outer edges having the second thickness different from the first thickness. The mechanical transducer failure detection module 140 and/or ultrasound operator may determine that the mechanical transducer 201 has malfunctioned if the artifacts 310 are not shown in the ultrasound image 300 and/or if the artifacts 310 are not shown at the appropriate position in the ultrasound image 300.

The ultrasound probe 200 illustrated in FIGS. 8 and 9 share various characteristics with the ultrasound probe 104 illustrated in FIG. 3 as described above.

Figure 10:
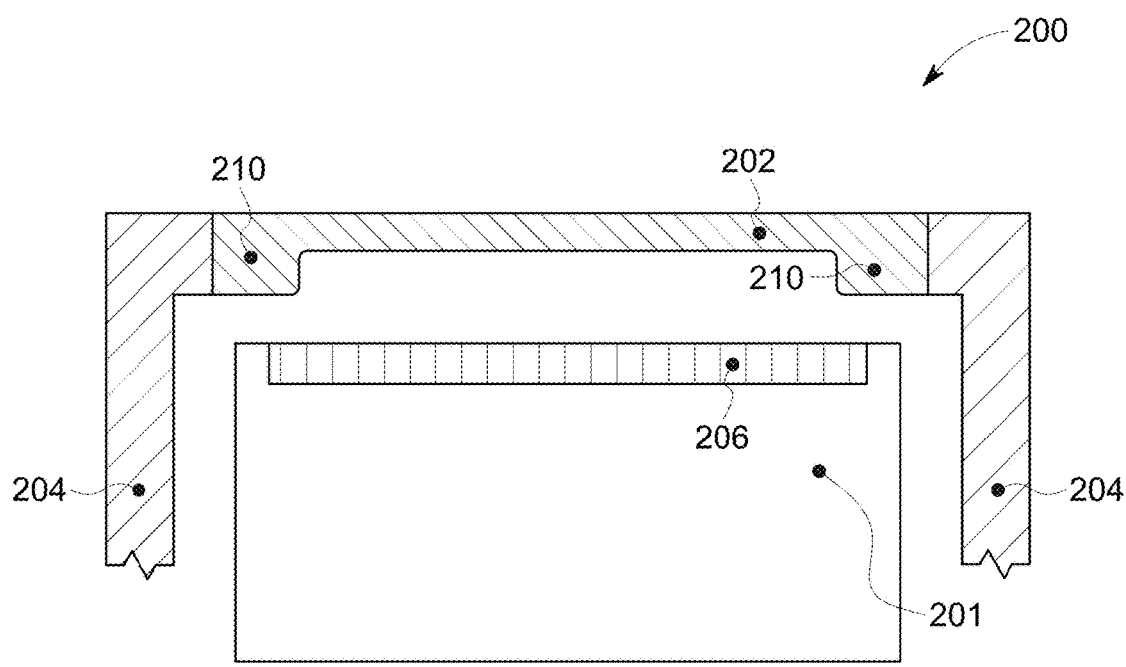
FIG. 10 illustrates a front cross-sectional view of an exemplary ultrasound probe having a probe cap with a defined structure, in accordance with various embodiments.

FIG. 10 illustrates a front cross-sectional view of an exemplary ultrasound probe 200 having a probe cap 202 with defined structures 210, in accordance with various embodiments. The front view of the ultrasound probe 200 in FIG. 10 is perpendicular to both the side views of ultrasound probes 200 in FIGS. 4, 5, and 8 and the top views of ultrasound probes 200 in FIGS. 6, 7, and 9. Referring to FIG. 10, the ultrasound probe 200 comprises a mechanical transducer 201 having transducer elements 206. The mechanical transducer 201 may be surrounded by and/or submerged in oil within a probe housing 204 and/or a probe cap 202. The mechanical transducer 201 is rotatable in a single plane in directions into and out of FIG. 10. The probe cap 202 comprises defined structures 210 at outer edges in at least a center acquisition plane of the mechanical transducer 201. The defined structures 210 may extend over to overlap laterally with at least a portion of the transducer elements 206 at the outer edges of the mechanical transducer 201 at least when the mechanical transducer 201 is at a center rotational position corresponding with the center acquisition plane of the mechanical transducer 201. The defined structures 210 may have first thickness and the remainder of the probe cap 202 may have a second, uniform thickness that is smaller than the first thickness. For example, the defined structures 210 may be protrusions, as shown in FIG. 3, having a larger thickness than the remainder of the probe cap 202. The protrusions 210 at the outer edges of the probe cap 202 may be various sizes and/or lengths as shown, for example, in FIGS. 7-9.

The different thickness of the defined structure 210 and the remainder of the probe cap 202 causes distinguishable artifacts to be provided in a close range of acquired ultrasound image data if the mechanical transducer 201 is provided at a rotational position such that the transducer elements 206 overlap with the defined structure 210. For example, if the mechanical transducer 201 is at a center rotational position, the acquired ultrasound data would include artifacts representative of the defined structure 210 at outer edges in the close range of a corresponding ultrasound image. Referring again to FIG. 12, the artifacts 310 at the outer edges of the ultrasound image 300 may correspond with the defined structure 210 having a first thickness and/or a transition from the defined structure 210 to a non-defined structure portion of the probe cap 202 at the outer edges having a second thickness different from the first thickness. The mechanical transducer failure detection module 140 and/or ultrasound operator may determine that the mechanical transducer 201 has malfunctioned if the artifacts 310 are not shown in the ultrasound image 300 and/or if the artifacts 310 are not shown at the appropriate position in the ultrasound image 300.

The ultrasound probe 200 illustrated in FIG. 10 may share various characteristics with the ultrasound probes 104, 200 illustrated in FIGS. 3, 5 and 7-9 as described above.

Referring again to FIGS. 4-10, the oil-filled distance between the inside of the probe cap 202 and the mechanical transducer 201 may be in a range from 0.2 mm to 1 mm. In various embodiments, the oil-filled distance between the inside of the probe cap 202 and the mechanical transducer may be greater than 1 mm. In a representative embodiment, the thickness of the probe cap 202 may be approximately 1 millimeter (defined as 0.5 mm to 2.5 mm). In an exemplary embodiment, the thickness of the defined structure 210 in the probe cap 202 may be approximately 0.3 mm (defined as 0.05 mm to 0.5 mm). In certain embodiments, the size of the step between the inside surface of the probe cap 202 and the inside surface of the defined structure 210 may pre-defined based on an anticipated quarter-wavelength ($\lambda/4$) of ultrasonic signals transmitted from the ultrasound probe 104. For example, depending on the mechanical details and type of ultrasound probe 104, 200, and assuming an ultrasound frequency of 3 MHz and a speed of sound through the oil of 1534 m/s, the size of the step in the probe cap 202 may be 0.1278 mm. The quarter-wavelength step between the defined structure 210 and the remainder of the probe cap 202 causes a destructive interference when half of the transmitted ultrasound wave hits the upper surface structure and the other half of the ultrasound wave hits the lower surface structure. The destructive interference is created by a 180 degree phase shift that extinguishes the reflective halves of the waves to provide strong distinguishable artifacts. Accordingly, the destructive interference may increase the precision of the determination of the rotational position of the mechanical transducer 201 by increasing the ability of the mechanical transducer failure detection module 140 and/or ultrasound operator to identify the artifacts 310 in the ultrasound image 300. As used herein, a defined structure 210 having a quarter-wavelength step distance is referred to as "a $\lambda/4$ structure."

Figure 13:
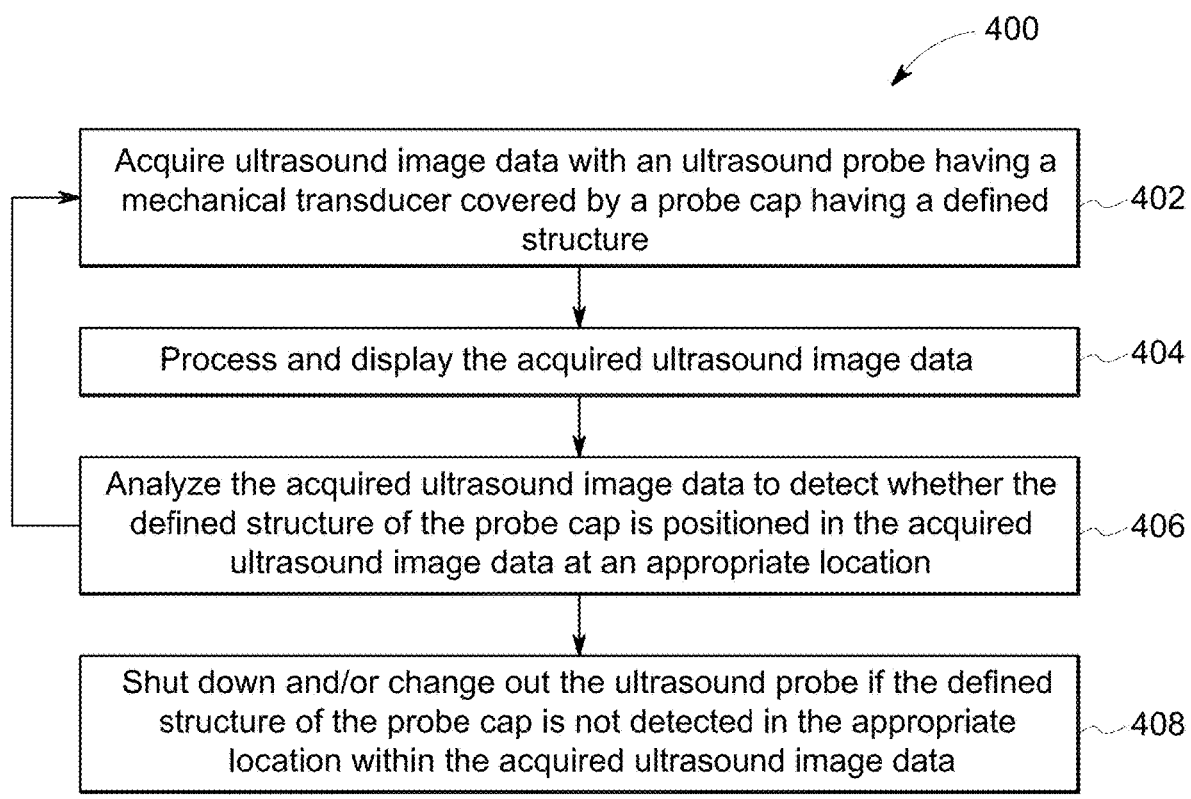
FIG. 13 is a flow chart illustrating exemplary steps that may be utilized for the detection of a failure of a mechanical ultrasound transducer assembly by analyzing artifacts in ultrasound images of a probe cap having a defined structure, in accordance with various embodiments.

FIG. 13 is a flow chart 400 illustrating exemplary steps 402-408 that may be utilized for detection of a failure of a mechanical ultrasound transducer assembly 104, 201, 203 by analyzing artifacts 310 in ultrasound images 300 of a probe cap 202 having a defined structure 210, in accordance with various embodiments. Referring to FIG. 13, there is shown a flow chart 400 comprising exemplary steps 402 through 408. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 402, a probe 104 of an ultrasound system 100 may acquire ultrasound image data with an ultrasound probe 104, 200 having a mechanical transducer 201 covered by a probe cap 202 having a defined structure 210. The ultrasound system 100 may acquire ultrasound data, for example, as described above with regard to FIG. 3 using a probe cap 202 described above with regard to one or more of FIGS. 4-10.

At step 404, a signal processor 132 of the ultrasound system 100 may process and display the acquired ultrasound image data. For example, the signal processor may process the ultrasound image data acquired at step 402 to generate ultrasound images 300 for presentation at a display system 134. In various embodiments, the ultrasound images 300 may include artifacts 310, 320 in a close range of the images 300 corresponding with the probe cap 202 and/or defined structure(s) 210 of the probe cap 202.

At step 406, the acquired ultrasound image data may be analyzed to detect whether the defined structure 210 of the probe cap 202 is positioned in the acquired ultrasound image data at an appropriate location. For example, a mechanical transducer failure detection module 140 of the signal processor 132 may apply image detection techniques and/or machine learning techniques to detect whether artifacts 310 corresponding to defined structure(s) 210 of the probe cap 202 are present in the ultrasound image 300 and the position of any detected artifacts 310. The mechanical transducer failure detection module 140 may compare the position(s) of detected artifacts 310 to stored reference location(s) to detect whether the defined structure 210 of the probe cap 202 is positioned in the ultrasound image 300 at the appropriate location corresponding with an appropriately positioned mechanical transducer 201. As another example, an ultrasound operator may visually detect whether the defined structure 210 of the probe cap 202 is positioned in an ultrasound image 300 presented at a display system 134 at the appropriate location. The ultrasound image 300 may allow the ultrasound operator to visually confirm the rotational position of the mechanical transducer 201 based on the artifacts 310 shown in the close range of the ultrasound image 300 presented at the display system 134.

At step 408, the ultrasound probe 104, 200 may be shut down and/or changed out if the defined structure 210 of the probe cap 202 is not detected in the appropriate location within the acquired ultrasound image data. The mechanical transducer 201 of the ultrasound probe 104, 200 may have experienced a mechanical and/or electrical failure if the mechanical transducer 201 is in an incorrect rotational position. The determination that the mechanical transducer 201 is incorrectly positioned may be based on whether artifacts 310 representative of the defined structure 210 of the probe cap 202 are detected in the correct position in the ultrasound image 300 at step 406. The mechanical transducer failure detection module 140 of the signal processor 132 may provide a transducer failure notification, shut off power provided to the ultrasound probe 104, 200, and/or otherwise disable the ultrasound probe 104, 200 in response to a determination that the mechanical transducer 201 is in an incorrect rotational position. Additionally and/or alternatively, the ultrasound operator may change out the ultrasound probe 104, 200 in response to the alerts, the disabling of the probe 104, 200, and/or the visual determination that the defined structure 210 of the probe cap is not in the appropriate location at step 406.

Aspects of the present disclosure provide an ultrasound probe 104, 200 comprising a mechanical transducer 201 rotatable about an axis 203. The mechanical transducer 201 may be operable to acquire ultrasound image data at one or more rotational positions of a plurality of rotational positions. The ultrasound probe 104, 200 may comprise a probe housing 204 having a probe cap 202 covering the mechanical transducer 201. The mechanical transducer 201 may be directed toward the probe cap 202 at each of the plurality of rotational positions. The probe cap 202 may comprise a defined structure 210 having a first thickness and a remainder portion having a second thickness different than the first thickness. At least a portion of the defined structure 210 may be at a center section of the probe cap 202 corresponding with a center rotational position of the mechanical transducer 201.

In a representative embodiment, the ultrasound image data 300 acquired by the mechanical transducer at the center rotational position may comprise first artifacts 310 created by defined reflections corresponding with the defined structure 210 at the center section of the probe cap 202, and second artifacts 320 created by remainder reflections corresponding with the remainder portion at the center section of the probe cap 202. In an exemplary embodiment, acquisition of the ultrasound image data 300 by the mechanical transducer 201 is prevented if the mechanical transducer 201 is not located at the center rotational position as determined by one or both of the first artifacts 310 being not present in the acquired ultrasound image data 300 or the first artifacts 310 being located in an incorrect location in the acquired ultrasound image data 300. In various embodiments, the defined structure 210 is a λ/4 structure.

In certain embodiments, the defined structure 210 is a groove having the first thickness that is smaller than the second thickness of the remainder portion. The groove 210 may be one or both of positioned to extend across at least a central portion of the center section of the probe cap 202, or positioned at one or both outer edges of the center section of the probe cap 202. In a representative embodiment, the defined structure 210 is a protrusion having the first thickness that is larger than the second thickness of the remainder portion. The protrusion 210 may be one or both of positioned to extend across at least a central portion of the center section of the probe cap 202, or positioned at one or both outer edges of the center section of the probe cap 202.

In an exemplary embodiment, the defined structure 210 is positioned to extend across both outer edges of one half of the probe cap 202. The defined structure 210 at each of the outer edges may transition to the remainder portion to define a step at the outer edges of the center section of the probe cap 202. Each of the steps may be in a mechanical transducer image acquisition plane if the mechanical transducer 201 is located at the center rotational position. In various embodiments, the defined structure 210 extends diagonally across the probe cap 202 such that at least a portion of the defined structure 210 is in a mechanical transducer image acquisition plane in any of the plurality of rotational positions. In certain embodiments, the defined structure 210 is positioned at an inside surface of the probe cap 202. In a representative embodiment, one or more of a distance between an inside of the probe cap 202 and the mechanical transducer 201 is in a range from 0.2 mm to 1 mm, the thickness of the remainder portion of the probe cap 202 is approximately 1 mm, and the thickness of the defined structure 210 in the probe cap 202 is approximately 0.3 mm.

Various embodiments provide a system 100 for detecting a failure of a mechanical ultrasound transducer assembly 201 by analyzing artifacts 310, 320 in ultrasound images 300 of a probe cap 202 having a defined structure 210. The system 100 comprises an ultrasound probe 104, 200 comprising a mechanical transducer 201 rotatable about an axis 203. The mechanical transducer 201 may be operable to acquire ultrasound image data at one or more rotational positions of a plurality of rotational positions. The ultrasound probe 104, 200 may comprise a probe housing 204 having a probe cap 202 covering the mechanical transducer 201. The mechanical transducer 201 may be directed toward the probe cap 202 at each of the plurality of rotational positions. The probe cap 202 may comprise a defined structure 210 having a first thickness and a remainder portion having a second thickness different than the first thickness. At least a portion of the defined structure 210 may be at a center section of the probe cap 202 corresponding with a center rotational position of the mechanical transducer 201. The system 100 comprises a processor 132, 140 that may be configured to process the ultrasound image data acquired by the mechanical transducer 201 to generate an ultrasound image 300. The processor 132, 140 may be configured to detect whether artifacts 310 corresponding to the defined structure 210 of the probe cap 202 are present at an appropriate location in the ultrasound image 300.

In a representative embodiment, the system 100 may comprise a display system 134 configured to present the ultrasound image 300 generated by the processor 132, 140. In certain embodiments, the artifacts 310 are located in a close range of the ultrasound image 300. In an exemplary embodiment, the processor 132, 140 may be configured to disable the ultrasound probe 104, 200 if the artifacts 310 corresponding to the defined structure 210 are not present at the appropriate location in the ultrasound image 300. In various embodiments, the defined structure 210 is a λ/4 structure. In certain embodiments, the defined structure 210 is a groove having the first thickness that is smaller than the second thickness of the remainder portion. The groove 210 may be one or both of positioned to extend across at least a central portion of the center section of the probe cap 202, or positioned at one or both outer edges of the center section of the probe cap 202. In a representative embodiment, the defined structure 210 is a protrusion having the first thickness that is larger than the second thickness of the remainder portion. The protrusion 210 may be one or both of positioned to extend across at least a central portion of the center section of the probe cap 202, or positioned at one or both outer edges of the center section of the probe cap 202.

In an exemplary embodiment, the defined structure 210 is positioned to extend across both outer edges of one half of the probe cap 202. The defined structure 210 at each of the outer edges may transition to the remainder portion to define a step at the outer edges of the center section of the probe cap 202. Each of the steps may be in a mechanical transducer image acquisition plane if the mechanical transducer 201 is located at the center rotational position. In various embodiments, the defined structure 210 extends diagonally across the probe cap 202 such that at least a portion of the defined structure 210 is in a mechanical transducer image acquisition plane in any of the plurality of rotational positions. In certain embodiments, one or more of a distance between an inside of the probe cap 202 and the mechanical transducer 201 is in a range from 0.2 mm to 1 mm, the thickness of the remainder portion of the probe cap 202 is approximately 1 mm, and the thickness of the defined structure 210 in the probe cap 202 is approximately 0.3 mm.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled, or not enabled, by some user-configurable setting.

Other embodiments of the disclosure may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for detecting a failure of a mechanical ultrasound transducer assembly by analyzing artifacts in ultrasound images of a probe cap having a defined structure.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

The present disclosure may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:
1. An ultrasound probe comprising:
   a mechanical transducer rotatable about an axis, the mechanical transducer operable to acquire ultrasound image data at one or more rotational positions of a plurality of rotational positions; and
   a probe housing having a probe cap covering the mechanical transducer, wherein:
      the mechanical transducer is directed toward the probe cap at each of the plurality of rotational positions,
      the probe cap comprises a defined structure having a first thickness and a remainder portion having a second thickness different than the first thickness, and
      at least a portion of the defined structure is at a center section of the probe cap corresponding with a center rotational position of the mechanical transducer, wherein the ultrasound image data acquired by the mechanical transducer at the center rotational position comprises:
   first artifacts created by defined reflections corresponding with the defined structure at the center section of the probe cap, and
   second artifacts created by remainder reflections corresponding with the remainder portion at the center section of the probe cap.

2. The ultrasound probe of claim 1, wherein acquisition of the ultrasound image data by the mechanical transducer is prevented if the mechanical transducer is not located at the center rotational position as determined by one or both of the first artifacts being not present in the acquired ultrasound image data or the first artifacts being located in an incorrect location in the acquired ultrasound image data.

3. The ultrasound probe of claim 1, wherein the defined structure is a λ/4 structure.

4. The ultrasound probe of claim 1, wherein the defined structure is a groove having the first thickness that is smaller than the second thickness of the remainder portion, and wherein the groove is one or both of:
   positioned to extend across at least a central portion of the center section of the probe cap, or
   positioned at one or both outer edges of the center section of the probe cap.

5. The ultrasound probe of claim 1, wherein the defined structure is a protrusion having the first thickness that is larger than the second thickness of the remainder portion, and wherein the protrusion is one or both of:
   positioned to extend across at least a central portion of the center section of the probe cap, or
   positioned at one or both outer edges of the center section of the probe cap.

6. The ultrasound probe of claim 1, wherein the defined structure is positioned to extend across both outer edges of one half of the probe cap, the defined structure at each of the outer edges transitioning to the remainder portion to define a step at the outer edges of the center section of the probe cap, and wherein each of the steps are in a mechanical transducer image acquisition plane if the mechanical transducer is located at the center rotational position.

7. The ultrasound probe of claim 1, wherein the defined structure extends diagonally across the probe cap such that at least a portion of the defined structure is in a mechanical transducer image acquisition plane in any of the plurality of rotational positions.

8. The ultrasound probe of claim 1, wherein the defined structure is positioned at an inside surface of the probe cap.

9. The ultrasound probe of claim 1, wherein one or more of:
   a distance between an inside of the probe cap and the mechanical transducer is in a range from 0.2 mm to 1 mm,
   the thickness of the remainder portion of the probe cap is approximately 1 mm, and
   the thickness of the defined structure in the probe cap is approximately 0.3 mm.

10. A system comprising:
   an ultrasound probe comprising:
      a mechanical transducer rotatable about an axis, the mechanical transducer operable to acquire ultrasound image data at one or more rotational positions of a plurality of rotational positions; and
      a probe housing having a probe cap covering the mechanical transducer, wherein:
         the mechanical transducer is directed toward the probe cap at each of the plurality of rotational positions,
         the probe cap comprises a defined structure having a first thickness and a remainder portion having a second thickness different than the first thickness, and
         at least a portion of the defined structure is at a center section of the probe cap corresponding with a center rotational position of the mechanical transducer; and
   a processor configured to:
      process the ultrasound image data acquired by the mechanical transducer to generate an ultrasound image; and
      detect whether artifacts corresponding to the defined structure of the probe cap are present at an appropriate location in the ultrasound image.

11. The system of claim 10, comprising a display system configured to present the ultrasound image generated by the processor.

12. The system of claim 10, wherein the artifacts are located in a close range of the ultrasound image.

13. The system of claim 10, wherein the processor is configured to disable the ultrasound probe if the artifacts corresponding to the defined structure are not present at the appropriate location in the ultrasound image.

14. The system of claim 10, wherein the defined structure is a λ/4 structure.

15. The system of claim 10, wherein the defined structure is a groove having the first thickness that is smaller than the second thickness of the remainder portion, and wherein the groove is one or both of:
   positioned to extend across at least a central portion of the center section of the probe cap, or
   positioned at one or both outer edges of the center section of the probe cap.

16. The system of claim 10, wherein the defined structure is a protrusion having the first thickness that is larger than the second thickness of the remainder portion, and wherein the protrusion is one or both of:
   positioned to extend across at least a central portion of the center section of the probe cap, or
   positioned at one or both outer edges of the center section of the probe cap.

17. The system of claim 10, wherein the defined structure is positioned to extend across both outer edges of one half of the probe cap, the defined structure at each of the outer edges transitioning to the remainder portion to define a step at the outer edges of the center section of the probe cap, and wherein each of the steps are in a mechanical transducer image acquisition plane if the mechanical transducer is located at the center rotational position.

18. The system of claim 10, wherein the defined structure extends diagonally across the probe cap such that at least a portion of the defined structure is in a mechanical transducer image acquisition plane in any of the plurality of rotational positions.

19. The system of claim 10, wherein one or more of:
   a distance between an inside of the probe cap and the mechanical transducer is in a range from 0.2 mm to 1 mm,
   the thickness of the remainder portion of the probe cap is approximately 1 mm, and the thickness of the defined structure in the probe cap is approximately 0.3 mm.

\* \* \* \* \*